US005770149A

United States Patent [19]
Raible

[11] Patent Number: 5,770,149
[45] Date of Patent: Jun. 23, 1998

[54] EXTRACORPOREAL BLOOD OXYGENATION SYSTEM HAVING INTEGRATED BLOOD PUMP, HEAT EXCHANGER AND MEMBRANE OXYGENATOR

[75] Inventor: Donald A. Raible, Santa Ana, Calif.

[73] Assignee: Baxter International, Deerfield, Ill.

[21] Appl. No.: 551,256

[22] Filed: Oct. 31, 1995

[51] Int. Cl.[6] .................................................... A61M 1/14
[52] U.S. Cl. .............................................. 422/46; 422/48
[58] Field of Search ............... 422/46, 48; 261/DIG. 28; 210/645, 175, 195.2, 198.1; 604/4; 128/DIG. 3

[56] References Cited

U.S. PATENT DOCUMENTS

| | | | |
|---|---|---|---|
| 4,876,066 | 10/1989 | Bringham et al. | 422/46 |
| 4,975,247 | 12/1990 | Badolato et al. | 422/48 |
| 5,217,689 | 6/1993 | Raible | 422/46 |
| 5,266,265 | 11/1993 | Raible | 422/46 |
| 5,270,005 | 12/1993 | Raible | 422/46 |
| 5,290,236 | 3/1994 | Mathewson | 604/131 |
| 5,360,317 | 11/1994 | Clausen et al. | 415/206 |
| 5,368,438 | 11/1994 | Raible | 415/74 |
| 5,411,706 | 5/1995 | Hubbard et al. | 422/46 |
| 5,458,459 | 10/1995 | Hubbard et al. | 415/206 |
| 5,501,574 | 3/1996 | Raible | 415/74 |

FOREIGN PATENT DOCUMENTS

| | | |
|---|---|---|
| 0320815 | 6/1989 | European Pat. Off. . |
| 6-22619 | 3/1994 | Japan . |

*Primary Examiner*—Nina Bhat
*Attorney, Agent, or Firm*—Guy L. Cumberbatch; Robert D. Buyan

[57] ABSTRACT

An extracorporeal blood oxygenation system comprising an integrated blood pump/heat exchanger/membrane oxygenator assembly which is mountable upon, and engageable with, a separate motor/drive assembly. The blood pump of the system incorporates a novel axial/centrifugal impeller assembly. An optional blood reservoir may be incorporated into the system to receive and contain venous return and/or surgical site blood. Also, an optional arterial filter may be incorporated into the system for filtering the oxygenated blood before the blood is returned to the patient. The pump/heat exchanger/membrane oxygenator component is preferably constructed such that heat exchange fluid which is being infused into the heat exchanger will pass through and/or in contact with a portion of the membrane oxygenator so as to further maintain the temperature of blood as it passes through the membrane oxygenator.

28 Claims, 6 Drawing Sheets

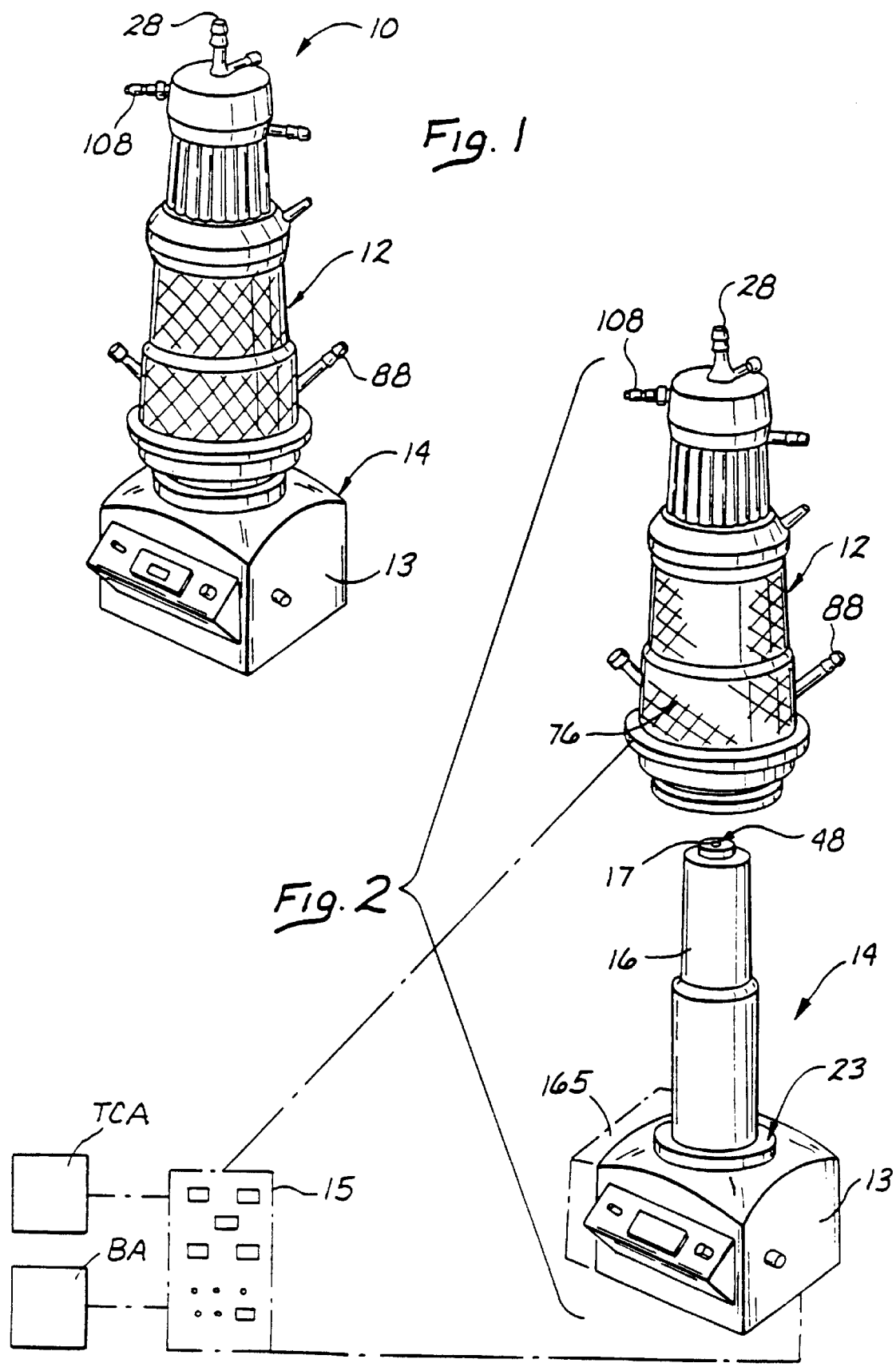

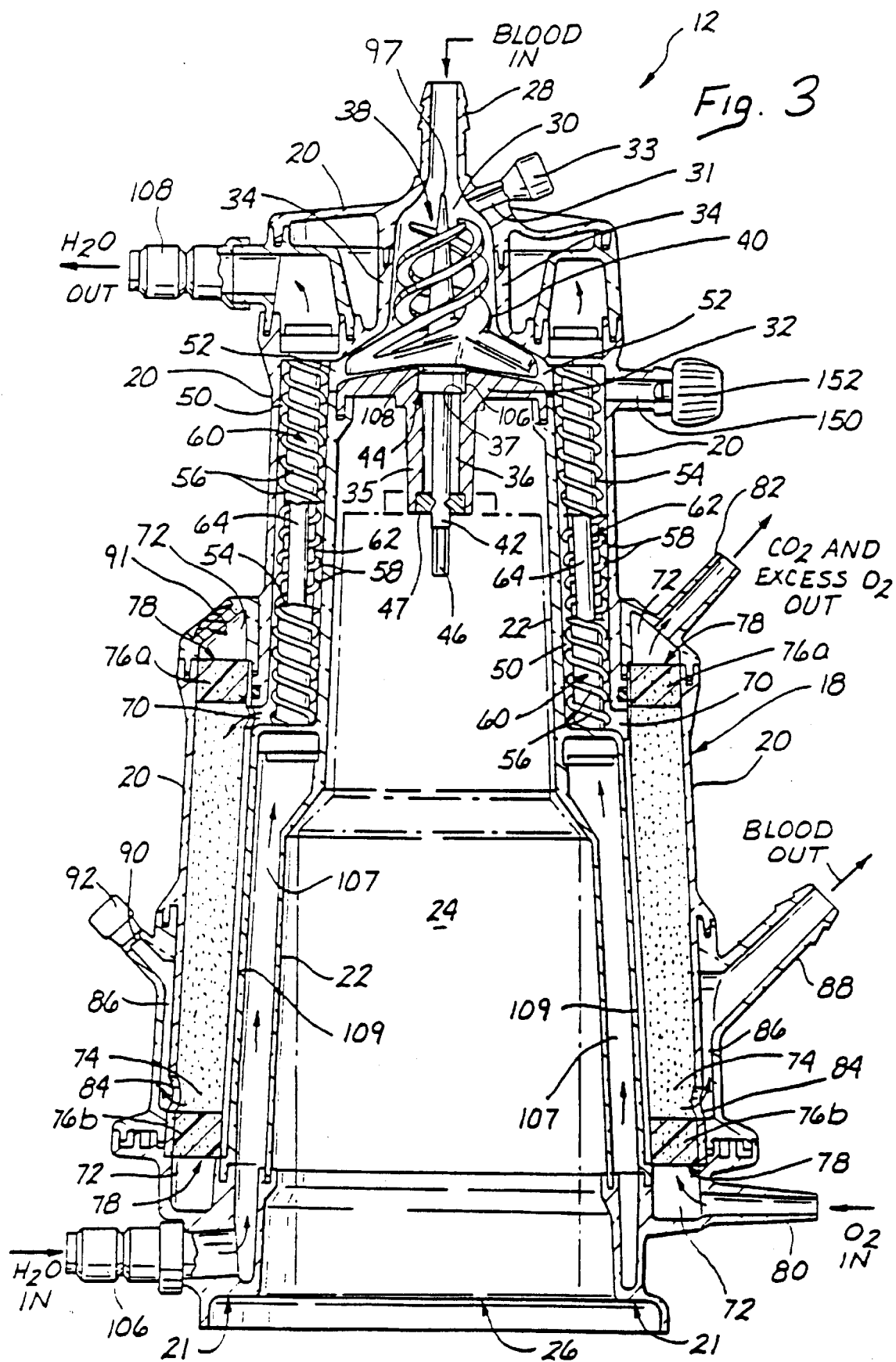

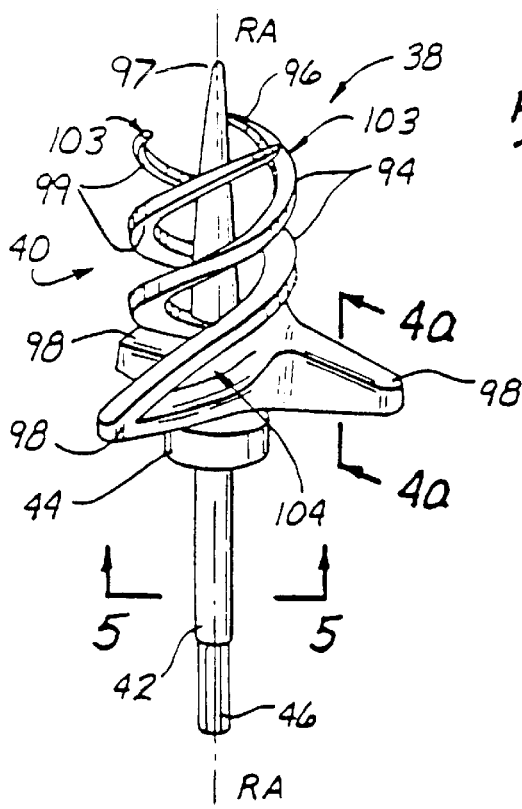
Fig.4
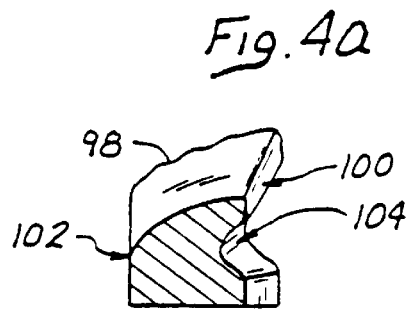
Fig.4a
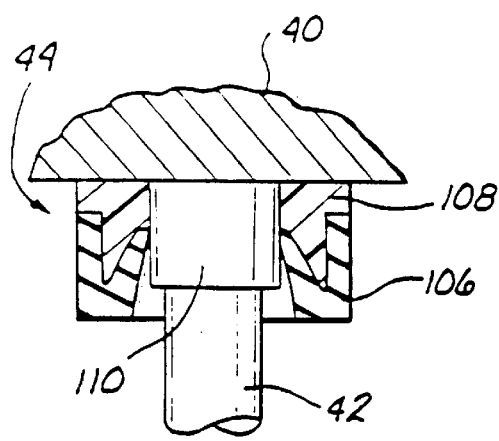
Fig.5
Fig.6
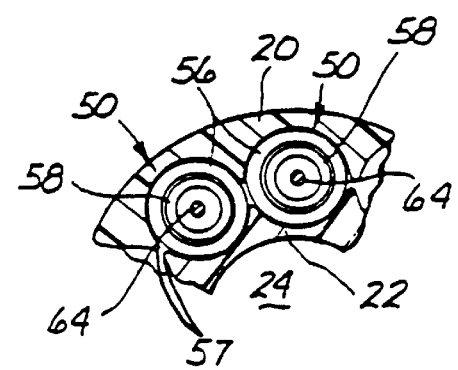
Fig.7

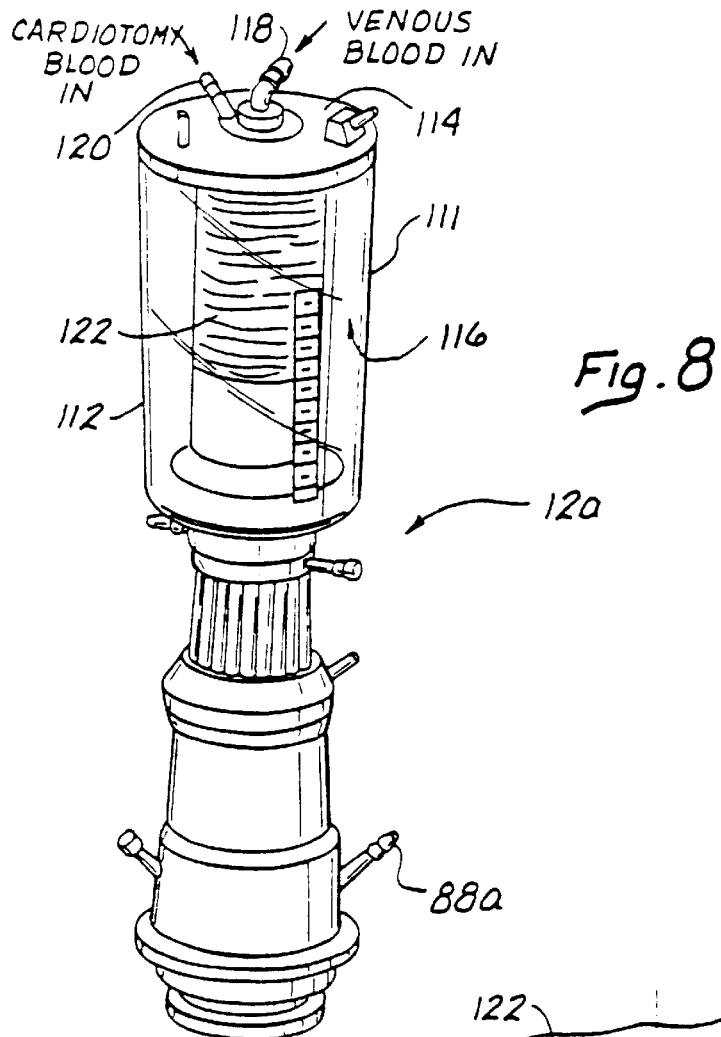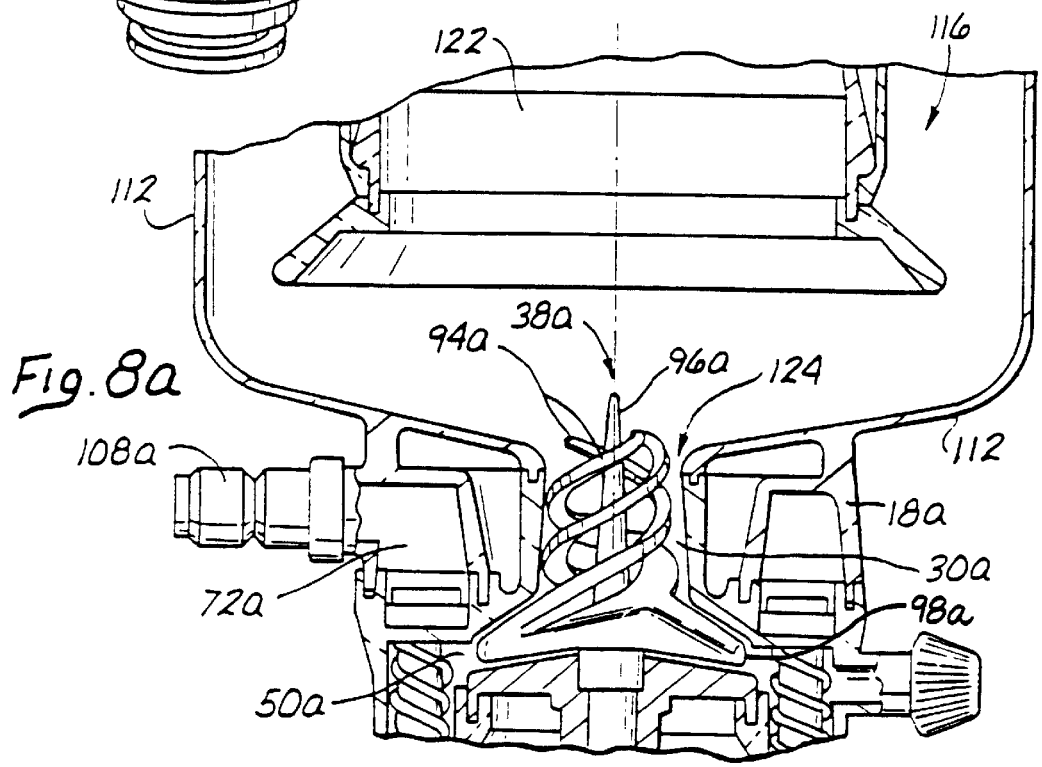
Fig. 8
Fig. 8a

EXTRACORPOREAL BLOOD OXYGENATION SYSTEM HAVING INTEGRATED BLOOD PUMP, HEAT EXCHANGER AND MEMBRANE OXYGENATOR

FIELD OF THE INVENTION

The present invention relates generally to extracorporeal blood treatment methods and devices, and more particularly to a new extracorporeal blood oxygenation system useable to provide cardiopulmonary support for patients who are undergoing major cardiothoracic surgical procedures or whose lungs are temporarily incapable of providing sufficient blood oxygenation due to injury or disease.

BACKGROUND OF THE INVENTION

Numerous extracorporeal blood oxygenation systems have heretofore been known for pumping, oxygenating and controlling the temperature of a patient's blood during major cardiothoracic surgical procedures and sometimes for temporary support of patients whose lungs are injured or diseased. The extracorporeal blood oxygenation systems of the prior art typically comprise four major components—a) a blood reservoir for collecting and defoaming venous blood and/or blood which has been reclaimed from a surgical site (e.g., cardiotomy blood), b) a heat exchanger for adjusting and controlling the temperature of the blood, c) an oxygenator for passing oxygen into and removing carbon dioxide from the blood and d) a blood pump for propelling the blood through the extracorporeal circuit, and through the patient.

In many of the previous extracorporeal membrane oxygenation systems, a heat exchanger, membrane oxygenator and blood pump were separately located on a pump/control console. Such pump/control console was usually situated some distance away from the patient, and was connected to the patient by way of lengthy blood-filled flexible tubes. However, the extension of such lengthy blood-filled tubes from the patient to a remotely located pump/control console was found to be less than desirable due to the fact that such lengthy, blood filled tubes would significantly increase the priming volume of the extracorporeal circuit and dilution of patient's blood which was required to fill the extracorporeal circuit during operation of the system. Also, such tubes were prone to being stepped upon, kinked, tripped over or accidentally disrupted, especially when such tubes were extended across the floor of a busy operating room.

Recent, efforts have been made to design integrated blood oxygenation systems wherein two or more of the system components (i.e., reservoir, heat exchanger, oxygenator, pump) are incorporated into a single integrated structure which may be positioned close to the patient, thereby eliminating or minimizing the need for the extension of lengthy blood-filled tubes to a remote location. Examples of membrane oxygenation systems which have incorporated two or more of the system components within a single integrated structure include those described in U.S. Pat. Nos. 5,270,005 (Raible); 4,975,247 (Badolato et al.); 5,217,689 (Raible); 5,266,265 (Raible); 5,368,438 (Raible); European Patent Application No. 0 320 815 A2 (Dideco S.p.A); Japanese Kokai Patent Application No. Hei 6[1994]-22619.

There remains a need in the art for the development of new and improved integrated extracorporeal blood oxygenation systems which are more reliable, and/or less expensive and associated with fewer drawbacks and/or complications, than those which have heretofore been known.

SUMMARY OF THE INVENTION

The present invention is an extracorporeal blood oxygenation system which basically comprises a) an integrated blood pump/heat exchanger/membrane oxygenator component and b) a motor/drive component. The integrated blood pump/heat exchanger/membrane oxygenator component comprises a blood pump, a heat exchanger positioned below said blood pump and a membrane oxygenator positioned below said heat exchanger. The blood pump, heat exchanger and membrane oxygenator are rigidly joined to one another, to form an integrated unitary assembly, said assembly having a blood inlet port for passing blood into the blood pump, a blood outlet port for allowing blood to pass out of the membrane oxygenator, and a blood flow path defined therewithin such that blood which enters the blood inlet port will pass initially through said pump, then through said heat exchanger, and then through said membrane oxygenator. The preferred direction of blood flow through the pump/heat exchanger/membrane oxygenator component is top to bottom, while the preferred directions of gas flow and heat-exchange-fluid flow is bottom to top. The blood pump/heat exchanger/membrane oxygenator component has an opening formed in it's bottom end, which leads into a hollow inner cavity defined therewithin. The motor/drive component of the system comprises a base housing having an electric motor located therewithin and a support projection which extends upwardly from said base housing. The support projection is sized and configured to insert through the bottom opening of, and upwardly into the hollow inner cavity of, the blood pump/heat exchanger/membrane oxygenator component. A rotatable drive member extends upwardly through the support projection and is engagable with the blood pump when the blood pump/heat exchanger/membrane oxygenator component is operatively mounted on the motor/drive component so as to rotatably drive the blood pump.

The system of the present invention may incorporate a novel blood pump having an axial-centrifugal pump impeller. Such axial-centrifugal pump impeller comprises a plurality of centrifugal propulsion legs which extend outwardly from a vertical rotational axis, each of said centrifugal propulsion legs having a leading surface and a trailing surface. A plurality of helical strut members or vanes are continuous with and, extend from, said centrifugal propulsion legs and are helically disposed about the vertical rotational axis of the impeller. A central member, such as a blunt conical or tapered elongate member, may extend co-axially with the rotational axis of the impeller, above the centrifugal propulsion legs, to form a central member about which the helical vanes are helically disposed. Such helical vanes are preferably formed upon and extend upwardly from the centrifugal propulsion legs, and are helically disposed or entwined about, but spaced outwardly away from, the vertical rotational axis of the impeller. Each helical vanes preferably has an undersurface, and the respective undersurfaces of the helical vanes are preferably in parallel relation to one another. Each helical vanes is preferably free-standing and unconnected to the other helical vanes and/or portions of the impeller, except for their basal points of attachment to the centrifugal propulsion legs of the impeller. Preferably, the helical vanes are coextensive with one another and their upper ends terminate adjacent one another so as to form a circular array, each of said upper ends of said helical vanes being spaced equidistantly from the vertical rotational axis of the impeller. Grooves or indentations may be formed in the leading surfaces of the centrifugal propulsion legs, in direct alignment with the undersurfaces of the respective helical vanes such that, as the impeller rotates, blood may be axially drawn by the helical vanes, and deposited within such grooves or indentations and ahead of the leading surfaces of the centrifugal propulsion legs. The rotating centrifugal propulsion legs or spreader star will then spread the blood, radially outward, such that the blood will flow from the blood pump housing, into the heat exchanger.

The heat exchanger portion of the system may comprise a housing which defines a generally cylindrical heat exchange cavity wherein a plurality of heat exchange tubes are vertically disposed. Such heat exchange tubes may be twisted to increase the surface area for heat transfer such that helical ribs are formed on the inner and outer surfaces of the tubes, providing helical troughs through which blood may flow around the tubes and between the adjacent inner and outer walls of the heat exchanger housing. Rigid rod members may extend co-axially through the lumens of the heat exchange tubes to prevent heat exchange fluid from flowing laminarly through the center of each tube and, instead, requiring the heat exchange fluid to flow around such rod members, and in contact with the inner surfaces of the heat exchange tubes thereby resulting in increased heat transfer. Blood emanating from the blood pump flows downwardly and helically around the helical outer troughs of the individual heat exchange tubes, thereby effecting temperature control of the flowing blood. The housing walls of the heat exchanger portion of the system may be scalloped or otherwise configured to substantially surround each heat exchange tube and to abut against the outer helical ribs formed on each tube. Such heat exchange housing configuration will channel the downwardly flowing blood into the outer helical troughs of the heat exchange tubes.

The membrane oxygenator portion of the system may comprise a generally cylindrical gas exchange cavity wherein a plurality of tubular gas exchange membranes are disposed. Gas inlet and outlet ports are connected to the opposite ends of the tubular hollow fiber membranes to facilitate passage of gas through the lumens of the membranes. Blood which has passed through the heat exchanger flows downwardly through the gas exchange cavity wherein the blood is distributed radially onto and in contact with the outer surfaces of the tubular gas exchange membranes. In this regard, $O_2$ and $CO_2$ are exchanged between the blood and the gas which is passing or being transported through the tubular gas exchange membranes. The heat exchange fluid which flows through the tubes of the heat exchanger may initially flow through a passageway formed within or adjacent to the membrane oxygenator portion of the system such that the entering heat exchange fluid will additionally cause warming or cooling of the blood as it passes through the membrane oxygenator portion of the system, thereby enhancing the overall blood temperature control which is maintained as the blood passes through the system. In this regard, a cylindrical heat exchange fluid flow space may be formed on the inner surface of the membrane oxygenator portion of the system, with one or more walls or heat transfer surfaces.

The system of the present invention may optionally incorporate a flexible or rigid blood reservoir, preferably mounted on top of the blood pump, to receive and collect venous and/or surgical site blood. Such blood reservoir may incorporate a filter and/or defoamer for filtering and/or defoaming such blood prior to passage of the blood into the blood pump.

The system of the present invention may optionally incorporate an arterial filter, preferably mounted upon or adjacent to the membrane oxygenator. Such arterial filter will filter the blood after it has passed through the membrane oxygenator portion of the system, but before the blood is returned to the patient. A bypass valving apparatus may be incorporated for alternately a) shunting the flowing blood through the arterial filter or b) allowing the flowing blood to bypass the arterial filter.

The system of the present invention may optionally incorporate a battery mounted upon or associated with the motor/drive component, to provide emergency back-up power in the event that the electrical supply to the system is lost or disrupted.

The system of the present invention may be manually monitored and controlled by adjusting knobs, buttons, settings and/or by viewing read outs, gauges and indicia located on the various components of the system and/or on attendant devices such as the usual heat exchange fluid control apparatus and/or oxygen/air blending apparatus. Alternatively, however, a remote monitoring and/or control console may be provided at a single remote location whereby variables and parameters of the system may be monitored and/or the operation of the system (e.g., on/off, pump speed, heat exchange fluid temperature, heat exchange flow rate, $FiO_2$, gas flow rate, etc.) may be controlled. Such remote monitoring and/or control console may be connected to the system by way of one or more wires coupled to the input control buttons and switches of the system and/or to various sensors (e.g., pH, $pCO_2$, $pO_2$, flow rate, temperature) mounted at desired locations within the system.

Additional objects and advantages of the invention will become apparent to those skilled in the art upon reading and understanding of the following detailed description, and upon consideration of the accompanying drawings.

BRIEF DESCRIPTION OF THE DRAWINGS

FIG. 1 is a perspective view of an integrated extracorporeal blood oxygenation system of the present invention.

FIG. 2 is an exploded perspective view of the integrated extracorporeal blood oxygenation system of FIG. 1 including an optional remote monitoring/control computer and console.

FIG. 3 is a longitudinal sectional view of the pump/heat exchanger disk/membrane oxygenator blood component of the system shown in FIGS. 1 and 2.

FIG. 4 is a perspective view of the preferred pump impeller apparatus of the integrated blood pump/heat exchanger/membrane oxygenator component of the system shown in FIGS. 1, 2 and 3.

FIG. 4a is a partial cross sectional view through line 4a—4a of FIG. 4.

FIG. 5 is a bottom/cross sectional view through line 5—5 of FIG. 4.

FIG. 6 is an enlarged longitudinal sectional view showing the preferred pump shaft seal assembly of the pump impeller apparatus of FIG. 4.

FIG. 7 is a partial cross-sectional view through the heat exchanger portion of the preferred system.

FIG. 8 is a perspective view of an alternative blood reservoir/pump/heat exchanger/membrane oxygenator component of the system of the present invention.

FIG. 8a is a partial longitudinal sectional view through line 8a—8a of FIG. 8.

Figure 5A:
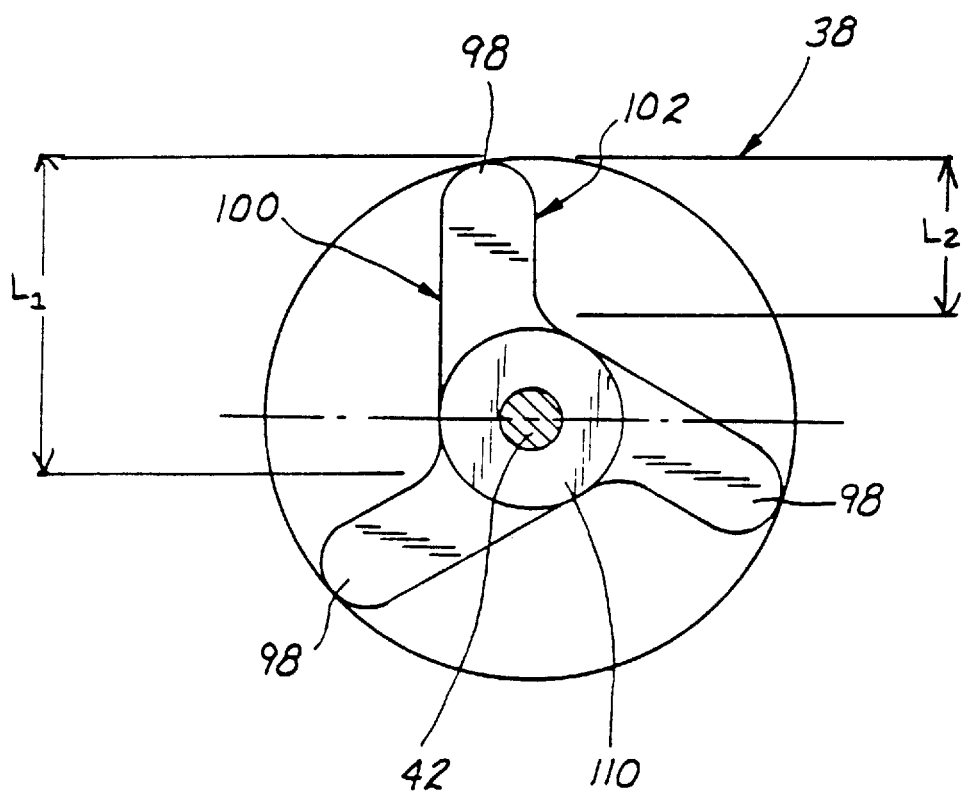
FIG. 5a is a schematic bottom/cross sectional view of the pump impeller of FIG. 4, showing dimensions and measurements of a presently preferred embodiment of the impeller.

DETAILED DESCRIPTION OF THE PREFERRED EMBODIMENTS i. General Structure of the Preferred Device

The following detailed description, and the accompanying drawings, are provided for purpose of describing and illustrating presently preferred embodiments of the invention only, and are not intended to limit the scope of the invention in any way.

FIGS. 1 and 2 provide a general, perspective view of a preferred extracorporeal blood oxygenation system 10 of the present invention. The preferred system 10, as shown, comprises an integrated pump/heat exchanger/membrane oxygenator component 12 (hereinafter refereed to as "P/HE/MO component") and a motor drive component 14 (hereinafter referred to as "M/D component"). The P/HE/MO component 12 is preferably constructed of materials which are suitable for disposal after a single use, while the M/D component 14 is preferably constructed of materials which are suitable for multiple use applications.

The M/D component 14, shown in FIG. 2, comprises an up-standing, stationary support member 16 having an annular shoulder 23 formed thereon, and having a rotatable drive member 17 extending upwardly therethrough. The rotatable drive member 17 is rotationally driven by an electric motor located within the base 13 of the M/D component 14. An engagement structure 48, such as a female hexagonal bore or a splined engagement bore, is formed within the upper end of the rotatable drive member 17.

The P/HE/MO component 12 is mountable upon the upstanding support member 16 of the M/D component 14, in the manner shown in FIG. 1. The preferred structure and assembly of the P/HE/MO component 12 is shown in detail in FIGS. 3–6.

With particular reference to FIGS. 3–6, the P/HE/MO component 12 may comprise a rigid housing 18 which includes an outer wall 20 and an inner wall 22. The housing 18 defines an elongate hollow inner cavity 24 which extends upwardly from an opening 26 formed in the bottom of the P/HE/MO component 12. The elongate, hollow inner cavity 24 of the P/HE/MO component 12 is sized and configured to receive therewithin, and rest upon, the upstanding support member 16 of the M/D component 14. In this regard, an annular shoulder 21 may be formed around the periphery of the opening 26 formed in the bottom end of the P/HE/MO component 12, and such annular shoulder 21 may abut against and rest upon a corresponding annular flange 23 formed at the base of the upstanding support member 16 of the M/D component 14. It will be appreciated by those skilled in the art that various types of locking mechanisms (not shown), such as a bayonet type locking system or mechanical latches may be provided to accomplish locking and holding of the P/HE/MO component 12 in a substantially fixed operational position upon the M/D component 14. However, in some embodiments of the invention such locking or latching mechanism may be unnecessary, and the desired positioning of the P/HE/MO component 12 upon the M/D component 14 may be achieved and maintained through precise configurational correspondence between the shape of the upstanding support member 16 and the shape of the inner housing wall 22 which defines the hollow inner cavity 24 of the P/HE/MO component 12.

When the P/HE/MO component 12 is mounted in its intended operative position upon the M/D component 14, the shaft engagement structure 46 of the drive member 17 will firmly engage the corresponding engagement structure 48 to provide sound rotatable driving of the pump impeller 40 within the impeller housing cavity 30.

In general, blood is caused to flow in a generally downward direction through the P/HE/MO component 12, while gas (e.g., oxygen or oxygen-enriched air) and heat exchange fluid (e.g., warm water) are caused to flow in a generally upward direction therethrough. Such counterdirectional flow of the blood relative the gas and heat exchange fluid will result in optimal gas-exchange and heat-exchange efficiency within the system 10. In this regard, a blood inlet port 28 is formed in the top of the P/HE/MO component 12 and provides a passageway through which leads into a pump impeller housing cavity 30. A bubble outlet port 31 having a threaded cap member 33 positioned thereon is located near the top of the pump impeller housing cavity 30, to permit any air bubbles which collect at the top of the pump impeller housing cavity 30 to be vented or aspirated and removed through such air bubble port 31.

The pump impeller housing cavity 30 is of a generally bell-shaped configuration, as shown, and is defined by a bottom wall 32 and a side wall 34. The side wall 34 of the pump impeller housing cavity 30 comprises an upper cylindrical portion of a first diameter, and a lower portion which slopes outwardly to a second, larger diameter. The outslopping bottom portion of the pump impeller housing cavity 30 is in open communication with an annular blood outflow space 52, through which blood may exit the impeller housing cavity 30.

A stepped bore 36 extends downwardly through the bottom wall 32 of the impeller housing cavity 30 and through a cylindrical boss 35 which extends downwardly from the center of the bottom wall 32, as shown. An annular shoulder 37 is formed at a first location, within the stepped bore 36.

The preferred pump impeller assembly 38 comprises an axial/centrifugal pump impeller 40, a drive shaft 42 and a seal assembly 44. The pump impeller assembly 38 is mounted such that the axial/centrifugal pump impeller 40 thereof resides within the impeller housing cavity 30, with the drive shaft 42 thereof extending downwardly through the stepped bore 36. The seal assembly 44 of the pump impeller assembly 38 is positioned within the larger diameter upper portion of the stepped bore 36 such that the bottom edge of the seal assembly 44 rests upon the annular shoulder 37 within the stopped bore 36, as shown in FIG. 3.

A shaft engagement structure 46, such as a male hexagonal member, or a splined engagement member is formed on the bottom end of the drive shaft 42 and protrudes out of and beneath the bottom end of the cylindrical boss 35. The shaft engagement structure 46 is thus rotatably engageable with the corresponding engagement structure 48 formed within the top end of the rotatable drive member 17 of the M/D component 14, to establish a torque connection whereby the pump impeller 40 may be rotatably driven by rotation of the drive member 17.

Ball bearings 47 are mounted within the cylidrical boss 35, as shown in FIG. 3, to facilitate rotation of the impeller drive shaft 42 therewithin.

The configuration and construction of the heat exchanger portion of the system 10 is most clearly shown in FIGS. 3 and 7. As shown, the outer housing wall 20 and inner housing wall 22 of the heat exchanger portion have corrugations of scallops formed on their inner surfaces such that peaks or projections 57 will protrude between the heat exchange tubes 54 and will seat upon and abut against the outer edges of the outer helical ribs 56 formed on the heat exchange tubes 54 as shown in FIG. 7. The inward, peaks or projections 57 of the outer 20 and inner 22 housing walls of the heat exchanger portion of the system 10 will thereby define a heat exchanger cavity 50 which comprises a series of parallel cylindrical spaces wherein the individual heat exchanger tubes 54 are located.

Each heat exchanger tube 54 preferably comprises a 3/8"–1/2" OD stainless steel tube which has been twisted about its longitudinal axis such that an outer helical fin or rib 56 is formed on the outer surface thereof in and an inner helical fin or rib 58 is formed on the inner surface thereof. In the preferred embodiment shown in the drawings there are a total of 16 heat exchange tubes 54 mounted within the heat exchanger housing portion, it will be appreciated however that the size and total number of the heat exchange tubes 54 may vary. In this regard, an outer helical trough 60 is defined between the adjacent convolutions of the outer helical rib 56 of each heat exchange tube 54, and inner helical trough 62 is defined between the adjacent convolutions of the inner helical rib 58 thereof. A cylindrical rod member 64 extends longitudinally through the lumen of each heat exchange tube 54 and is coaxially centered therewith, so as to occupy the central space within the lumen of each heat exchange tube 54, thereby preventing the flowing heat exchange fluid from remaining laminar within the center of each lumen and requiring, instead, that such heat exchange fluid undergo helical flow through the inner helical troughs 62 of the heat exchange tubes 54, thereby providing for efficient heat transfer through the walls of the heat exchange tubes 54.

A heat exchange liquid, such as warm water, may be passed into the inlet port 106, upwardly through cylindrical flow space 107, through the lumens of the heat exchange tubes 54, and out of outlet port 108. As the heat exchange fluid passes upwardly through the lumens of the heat exchange tubes 54, such heat exchange fluid will be prevented from undergoing laminar flow within the center of each lumen due to the presence of the elongate rod members 64 therein. As a result, the upwardly flowing heat exchanged liquid will be caused to circulate within the inner helical troughs 62 of the heat exchange tubes 64, thereby maximizing the contact of the heat exchange liquid with the heat exchange tubes 54 and causing the material of the heat exchange tubes 54 to become equilibrated with the temperature of the heat exchange liquid flowing therethrough.

Concurrently, blood which has entered the blood inlet port 28 at the top of the P/HE/MO component 12, will be axially and centrifugally propelled by pump impeller 40 and caused to flow outwardly from the impeller cavity 30, through the first annular blood outflow space 52, and into the top of the segmented heat exchange cavity 50. Thereafter, the blood will flow downwardly through the outer helical troughs 60 of the heat exchange tubes 54, coming into contact with the outer surfaces of the heat exchange tubes 54, such that the temperature of the flowing blood will become equilibrated with the temperature of the walls of the heat exchange tubes 54. In this manner, the temperature of the blood becomes adjusted to, and equilibrated with, the temperature of the heat exchange liquid which is being pumped through the tubes 54.

When the flowing blood reaches the bottom of the cylindrical heat exchange cavity 50 it passes outwardly through a second annular blood outflow space 70 and into a cylindrical gas-exchange cavity 72 which is located beneath, and slightly outboard of, the cylindrical heat exchange cavity 50. A multiplicity of gas exchange membranes 74 are packed or otherwise disposed within the gas-exchange cavity 72. Such gas exchange membranes 74 preferably comprise tubular gas exchange membranes of the type well known in the art. Such tubular gas exchange membranes are wound or otherwise deployed in parallel, non-parallel, crossing or non-crossing fashion within the cylindrical gas exchange cavity 72 of the oxygenator portion of the system 10, and the opposite ends of such tubular membranes 74 are embedded within annular rings of potting material 76a, 76b. Such potting material rings 76a, 76b are positioned adjacent the upper and lower ends of the cylindrical gas exchange cavity 72, as shown. The inner lumens of the tubular hollow fiber membranes open through the exposed outer surfaces 78 of the upper and lower potting material rings 76a, 76b. In this regard, as will be described more fully herebelow under the heading "Preferred Mode of Operation", oxygen or oxygen-enriched air may be passed into a gas inlet port 80 and, into the empty bottom portion of the cylindrical gas exchange cavity 72 such incoming gas will then flow, and into the lumens of the hollow fiber membranes 74 through the bottom lumenal openings which are embedded within the outer surface 78 of the lower potting material ring 76b. Thereafter, the gas will flow through the lumens of gas exchange fiber membranes 74 as the blood percolates or drains downwardly in contact with the outer surfaces of the gas exchange membranes 74. In this manner $O_2/CO_2$ exchange will occur between the gas and the blood. The gas (having received $CO_2$ from the blood, and retaining any excess $O_2$ which has not diffused into the blood), will then pass out of the upper ends of the lumens of the gas exchange membranes 74 located within the outer surface 78 of the upper potting material ring 76a, into the empty portion of the cylindrical gas exchange space above the outer surface 78 of the upper potting material ring 76a, and out of gas outlet port 82.

As shown in FIG. 3, the cylindrical heat exchange fluid flow space 107 which is formed inside of the membrane oxygenator portion of the system, is defined by the inner housing wall 22 of the membrane oxygenator portion, and an outer heat-transfer wall 109 which, in the preferred embodiment, is formed of a double-layer plastic wall wherein both layers of plastic are in direct abutting contact with each other. Heat exchange fluid (e.g., warm water) is passed into the heat exchange fluid inlet port 106, and flows upwardly through the cylindrical heat exchange fluid flow space 107, before entering the bottom ends of the heat exchange tubes 54 within the heat exchange portion of the system. As the heat exchange fluid passes upwardly through the heat exchange fluid flow space 107, temperature transfer will occur through the temperature transfer wall 109 of the heat exchange fluid flow space 107. Blood which is flowing downwardly through the cylindrical heat exchange cavity 72 is located on one side of the temperature transfer wall 109 while the upwardly flowing heat exchange fluid within flow space 107 is located on the other side of such temperature transfer wall 109. This arrangement results in continued temperature maintenance of the blood as the blood passes downwardly through the membrane oxygenator portion of the system, and prevents the blood from undergoing substantial heat loss as it passes downwardly through the membrane oxygenator portion of the system 10. Also, as described hereabove with respect to the heat exchanger portion of the system 10, the counterdirectional flow of the blood through the gas exchange cavity 72, relative to the flow of heat exchange fluid through the cylindrical heat exchange fluid flow space 107 provides for enhanced or optimal temperature exchange efficiency through temperature transfer wall 109.

The blood, after having passed over the outer surfaces of the hollow fiber membranes 74 within gas exchange cavity 72 and after having thereby lost $CO_2$ and received $O_2$, will then flow out of the bottom of the cylindrical gas exchange cavity 72, through outlet apertures 84, and into a blood outlet manifold 86. A blood outlet port 88 is formed in the blood outlet manifold 86. An arterial blood return tube may be connected to blood outlet port 88, such that the oxygenated blood from the system 10, may be carried through such tube, back to the vasculature of the patient.

A blood sample withdrawal port 90, having a threaded cap member 92 positionable thereon, is provided (as shown) to permit samples of the oxygenated blood to be withdrawn from the blood return manifold 86 for blood gas analysis or other purposes.

A pressure relief valve 91 is formed within the housing 18, in communication with the cylindrical gas-exchange cavity 72. Such pressure relief valve 91 may comprise an elastomeric diaphragm-type pressure relief valve, or any other suitable type of pressure relief apparatus, which will vent gas from the interior of the cylindrical gas exchange cavity 72 in the event that the gas pressure within the cavity 72 exceeds a predetermined maximum pressure.

A recirculation/emergency port 150 may be formed in the portion of the housing 18 which houses the heat exchange cavity 50 to permit blood to be infused directly into the top end of the cylindrical heat exchange cavity 50, thereby bypassing the blood pump of the integrated system 10. A fluid tight cap member 152 is positioned upon such recirculation/emergency port 150 to provide a fluid tight seal thereon. However, when it is desired to recirculate blood (e.g., prior to connection of the blood return line to the patient), a blood recirculation tube may be connected from the blood outlet port 88 to the recirculation/emergency port 150 to permit the blood to be recirculated through the heat exchanger and membrane oxygenator components of the system 10. Also, in the event that the motor or drive train of the M/D component 14, or the blood pump of the P/HE/MO component 12 should malfunction in a manner which renders the pumping apparatus incorporated within the system 10 ineffective or unusable, the blood return tube which had been attached to the blood inlet port 28 may be alternately connected to the recirculation/emergency port 150 and a separate pump (e.g., a peristaltic pump or centrifugal pump of the type known for pumping of blood through tubing) may be connected to or mounted on such blood return tube to provide the pumping force necessary to propel the blood through the system 10 and through the patient.

Optionally, one or more sensors (not shown) may be mounted at desired locations within the P/HE/MO component 12 and/or M/D component 14 to provide for monitoring of various operational parameters and variables such as blood pH, blood $pCO_2$, blood $pO_2$, blood temperature, blood flow rate(s), $FiO_2$, gas temperature, gas flow rate(s), gas $pO_2$, gas $pCO_2$, water temperature, water flow rate(s), pump rotational speed, electrical current flow to motor, etc. Such sensors (not shown) may be connected to one or more output displays to permit ongoing observation and monitoring of the operational parameters and variables of the system 10.

ii. Optional Remote Monitoring/Control Console

It will be appreciated that, operational control switches and/or monitoring displays may be located on the base 13 of the M/D component 14 and/or on the attendant devices such as the oxygen-air blending apparatus BA and/or the water temperature control apparatus TCA which are connected to the system 10. The operator of the system 10 may thus manually operate the control switches and monitoring displays of such individual components of the system to effect the desired operating of the system.

Alternatively, the operation of the system may be centrally controlled and/or monitored by connection of a remote monitoring and/or control console 15 to sensors (not shown) located within the P/HE/MO component 12 and or sensors/ controls switches located within the M/D component 14 and/or sensors/controls located within the separate water temperature control unit and/or sensor/controls located within the separate oxygen/air blending unit. The monitoring/control console 15 may incorporate various gauges, digital displays or other readouts for displaying the monitored operational variables and parameters, as well as various switches, knobs or other controls for energizing/de-energizing the system 10 and for controlling the other operational variables such as pump speed, water temperature, $FiO_2$, etc. It will be further appreciated that a computer may be incorporated into the monitoring and/or control console 15, and that such computer may be programmed to automatically monitor and control the operation of the system during predetermined types of procedures. Such computer may be provided with initial input of specific patient variables (e.g., height, weight, procedure type, etc.) and may calculate and derive, on the basis of such patient variables, the desired operational adjustments for the system 10 during the specific operative procedure to which the patient is being subjected.

iii. The Preferred Pump Impeller Assembly

The pump impeller assembly 38 is shown in detail in FIGS. 4–6. As shown, a preferred pump impeller assembly 38 comprises a central member 96, a plurality of outwardly extending centrifugal propulsion legs 98, and a plurality of helical vanes 94. A vertical axis of rotation RA is projectable through the impeller assembly as shown in FIG. 4. The helical vanes 94 are in parallel relation to one another and emanate separately from each of the centrifugal propulsion legs 98. The helical vanes are helically disposed around the central rotational axis RA. In the embodiment shown, the central member 96 has a blunt conical upper end portion 97, and is coaxial with the axis of rotation RA, in direct alignment with the blood inlet port 28 such that blood entering the blood inlet port 28 will impinge against the blunt conical end portion 97 of the central member 96 and will be thereby caused to flow outwardly into contact with the helical vanes 94. As the helical vanes 94 rotate, such strut members 94 will axially draw or pull the blood downwardly such that the blood will be deposited ahead of leading surfaces 100 (FIG. 5) of the centrifugal propulsion members 98 such that the blood will be centrifugally propelled by the rotating centrifugal propulsion legs 98 and caused to flow from the impeller cavity 30, through the first annular flow space 52 and into the segmented heat exchange cavity 50.

The helical vanes 94 are preferably arranged such that their undersurfaces 99 are parallel to one another and equidistantly spaced outboard of the central member 96. Each helical vanes 94 is individually formed and substantially freestanding and unconnected to any other portion of the impeller 40 except for its point of emanation or attachment from a respective one of the centrifugal propulsion legs 98 at the base of the impeller 40. The helical vanes 94 are preferably of equal length and are coextensive with one another such that their separate upper ends 103 are disposed in a substantially circular array about the blunt conical end portion 97 of the central member 96, as shown in FIG. 4.

As shown in FIGS. 4, 4a, 5 and 5a, each centrifugal propulsion leg 98 has a leading (i.e. frontal) surface 100 and a trailing (i.e. rear) surface 102. The length $L_1$ of the leading surface 108 of each centrifugal propulsion leg 98 is greater then the length $L_2$ of the trailing surface 102 thereof. In the preferred embodiment, the leading surface 100 of each centrifugal propulsion leg 98 has a length $L_1$ of approximately 1.24 cm while the trailing surface 102 of each such centrifugal propulsion leg 98 has a length $L_2$ of approximately 0.62 cm, as indicated on FIG. 5a. Blood receiving depressions or grooves 104 are formed in the leading surfaces 100 of the centrifugal propulsion legs 98, in direct alignment with the helical undersurfaces 99 of the helical vanes 94, thereby enhancing the volume of blood which may be deposited ahead of each leading surface 100 of each such centrifugal propulsion leg 98, and the resultant volume of blood which will be thereby centrifugally propelled, in a direction which is radial to the axis of rotation RA, and out of the first blood outflow space 52.

The impeller 40 is preferably formed of molded plastic such as ultra-high-density polyethylene or other plastic material which is available for direct blood contact. The impeller drive shaft 42 is inserted into a bore within the conical central member 96 and is firmly affixed thereto. Such drive shaft 42 may be formed of any suitable material, such as series 300 stainless steel or other metal. The hexagonal shaft engagement structure 46 formed on the lower end of the drive shaft 42 may be created by machining of the drive shaft 42 prior to its attachment to the impeller 40.

The preferred seal assembly 44 comprises a) an elastomeric, non-blood-contact, chevron-type seal 106 of the type commercially available as Part No. 343104 from the National Oil Seals Division of Federal Mogul Corporation, and b) a blood-contact-suitable ring member 108 which is positioned between the elastomeric seal 106 and the base of the impeller 40, and which is partially received and seated within the v-shaped annular grove of the chevron-type seal 106. This rigid seal ring member 108 is preferably formed of polytetrafluorethylene (Teflon™) or other material which is suitable for blood contact. In this regard, as shown in FIG. 3, the seal assembly 44 is operatively positioned such that only the rigid ring member 108 of the assembly 44 comes into contact with the patient's blood, insofar as a portion of such ring member 108 protrudes above the upper surface of the bottom wall 32 of the pump impeller cavity 30 and is thus exposed to the flowing blood. The elastomeric seal 106 portion of the assembly 44 is fully housed within the stepped bore 36 and does not come into contact with the patient's blood.

In the embodiment shown, a cylindrical flange 110 is formed on and extends downwardly from the base of the impeller 40, and the drive shaft 42 extends through the center of such flange 110. The seal assembly 44 is positioned such that the seal 106 rides on the outer surface of the cylindrical flange 110, rather than directly on the outer surface of the drive shaft 42 itself. It will be appreciated, however, that alternative modes of construction may be utilized wherein the seal 106 would ride directly against the outer surface of the drive shaft 42, to accomplish the desired liquid-tight sealing function.

By the above-summarized configuration and construction, the seal assembly forms a substantially fluid tight seal which prevents blood from leaking downwardly into the stepped impeller shaft bore 36, while allowing the entire impeller assembly 38 to freely rotate within bearings 47.

iv. Optional Blood Reservoir

Some embodiments of the invention may incorporate an optional blood reservoir formed as an integral part of the P/HE/MO component 12. FIGS. 8–8a show one such embodiment wherein there is provided a reservoir/pump/heat exchanger/membrane oxygenator component 12a (hereinafter referred to as the "R/P/HE/MO component"). In such embodiment, a flexible or rigid blood reservoir 111 is attached to or otherwise formed on top of the housing 18a. Such reservoir 111 receives venous return blood from the patient's vasculature and/or reclaimed blood from a surgical site (e.g., cardiotomy) sump or other source, and causes such venous and/or reclaimed blood to become pooled prior to allowing such blood to drain downwardly into the pump impeller housing cavity 30a and subsequently through the remainder of the system 10.

In the specific embodiment shown in FIGS. 8–8a, the blood reservoir 111 comprises a generally cylindrical outer wall 112 having a lid 114 positioned on top thereof, such that a hollow reservoir cavity 116 is defined therewithin. A venous blood return inlet 120 and a cardiotomy blood inlet 122 are formed in the lid 116 to permit venous return blood and cardiotomy blood to be passed into the inner cavity 116 of the reservoir 111. A defoamer/filter element 122 of the type well known in the art may be mounted within the cavity 116 such that the venous return and cardiotomy blood entering inlets 118 and 120 respectively will be received within the interior of the defoamer/filter element 122, and will percolate or flow outwardly therethrough, becoming thereby filtered and defoamed. The filtered and defoamed blood, which has percolated or flowed outwardly through the filter/defoamer element 122 will collect or pool within the hollow inner cavity 116 of the reservoir 111, and will then flow downwardly through outlet opening 124 at the base of the reservoir 111, entering directly into the upper cylindrical portion of the pump impeller housing cavity 30a. In this regard, when the pump impeller 40a of this embodiment is rotated in the first direction, the helical vanes 94a of the impeller 40a will draw blood downwardly from the inner cavity 116 of the reservoir 111 into the pump impeller cavity 30a, such that the blood will then be propelled by the leading edges of the impeller centrifugal propulsion legs 98a to flow outwardly through the annular blood outflow-space 50a, and to continue, thereafter, to flow through the system 10 in the manner described hereabove.

v. Optional Arterial Filter

Figure 9:
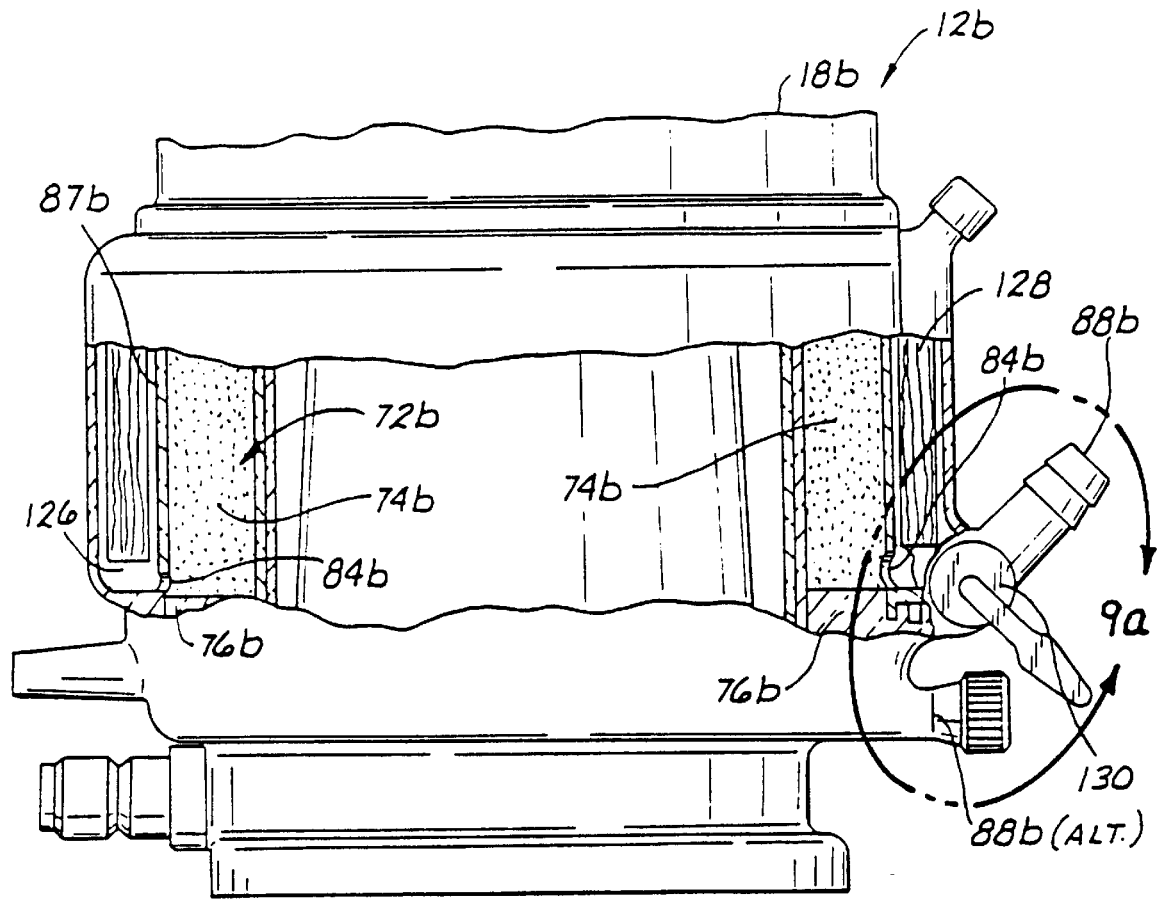
FIG. 9 is a partial perspective/cut-away view of a pump/heat exchanger/membrane oxygenator component (or reservoir/pump/heat exchanger/membrane oxygenator component) of the extracorporeal blood oxygenation system of the present invention, further incorporating an integrated arterial filter system.
Figure 9A:
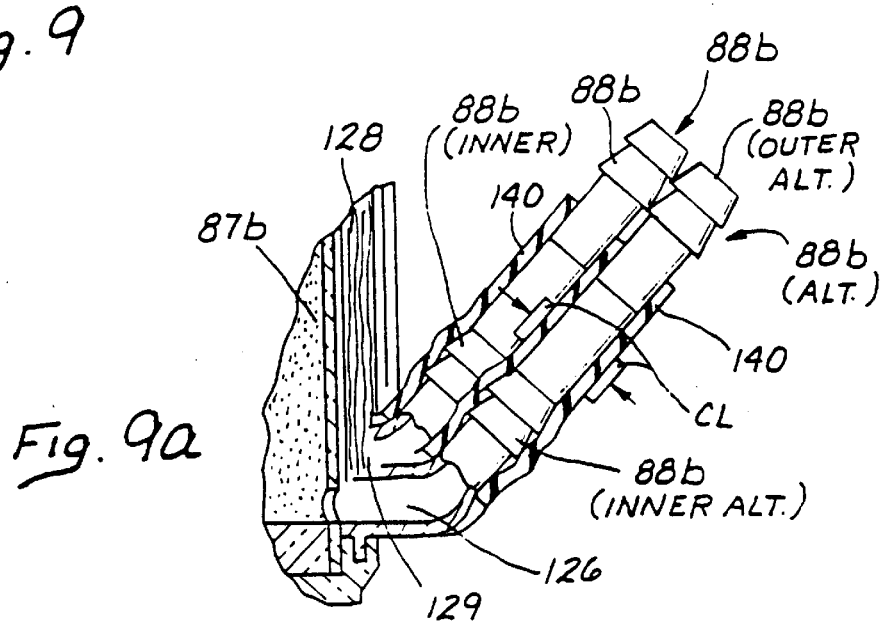
FIG. 9a is an alternative cross-sectional view of portion 9a of FIG. 9, showing an alternative blood outlet/valving apparatus.

Some embodiments of the invention may optionally include an arterial filter for filtering the blood after it has been oxygenated, but before it is returned to the patient. One example of an arterial filter apparatus 128 which may be integrated into the embodiment shown in FIGS. 9–9a is a woven polyester mesh material of 25–40 micron pore size (s), such as that which is commercially available from Tetko, Inc., 111 Calumet Street, Depew, N.Y. 14043. Additionally, any suitable rigid framework or structural matrix may be incorporated into the arterial filter apparatus 128 to hold and support the desired polyester mesh or other filtering material. In such embodiments incorporating an arterial filter, a portion of the housing 18b is modified such that the blood outlet manifold 86 is replaced by an arterial filter chamber 126 wherein the arterial filter apparatus 128 is positioned. A filtered blood outlet port 88b is provided to permit outflow of arterial blood which has passed through the filter apparatus 128. A non-filtered blood outlet port 88b(alt.) is also provided to permit outflow of arterial blood which has bypassed the filter apparatus 128. A valving apparatus 130, such as a stopcock, is incorporated into the filtered blood outlet port 88b. In this regard, when such valving apparatus 130 is in a first position, arterial blood will be permitted to flow through the arterial filter apparatus 128 and out of the filtered blood outlet port 88b. When the valving apparatus 130 is in a second (off) position, blood will be blocked from flowing through the arterial filter apparatus 128 or out of filtered blood outlet port 88b, and the blood will instead be diverted downwardly such that the blood will flow out of the alternative unfiltered blood outlet port 88b (alt.). Thus, the operator may volitionally bypass the arterial filter system at any time by simply closing the valving apparatus 130, and connecting the blood return tube to the alternative unfiltered blood outlet port 88b (alt.).

An alternative construction is shown in FIG. 9a wherein the filtered blood outlet 88b comprises a rigid inner blood outlet port 88b (inner) and a rigid tubular outer blood outlet port 88b (outer), with a segment of flexible tubing 140 disposed therebetween. Similarly, the alternative unfiltered blood outlet port 88b (alt.) comprises an inner tubular alternative outlet port 138b (inner-alt.) and an outer tubular alternative outlet port 88b (outer-alt.) when a clamp CL is applied to the flexible tubing segment 140 of the alternative unfiltered blood outlet port 88b (alt.), the arterial blood will pass through the arterial filter apparatus 128 and out of the filtered blood outlet port 88b. When it is desired to bypass the arterial filter apparatus 128, the clamp CL will be applied to the flexible tubing segment 140 of the filtered arterial blood outlet 88b, thereby blocking the flow of blood through the arterial filter apparatus 28 and/or out of the filtered blood outlet port 88b. As a result, the blood will bypass the arterial filter apparatus 128, and will flow out of the alternative unfiltered blood outlet port 88b (alt.).

vi. Optional Battery For Emergency Power

Optionally, some embodiments of the invention may also incorporate a battery pack 165 wherein a battery, such as a rechargeable-type battery, may be incorporated into the system 10 to provide operational power to the system 10 in the event that the usual alternating current suppy received by the system through a typical power cord, is interrupted or lost. As shown in FIG. 2, such optional battery pack 165 may be attachable to the base 13 of the M/D component 14, and may be readily interchangeable such that such battery pack 165 can be easily removed and replaced. It is preferable that the rechargeable battery located within the battery pack 165 be connected to a charging circuit whereby the battery will be continually or intermittently charged during routine operation of the system 10 using alternating current received through a wall outlet or other appropriate current source.

vii. Preferred Mode of Operation

When used for cardiopulmonary bypass during a cardiothoracic surgical procedure, the system 10 may be mounted on a ring stand or other appropriate mounting structure positioned close (e.g., within three feet of) the operating table upon which the patient is positioned. A venous blood return tube will be connected to the blood inlet port 28 (or to the venous inlet port 118 of any incorporated blood reservoir component 111, such as is shown in FIG. 8). A blood return tube will be connected from the then-operational blood outlet port 88, 88b, 88b (outer) or 88b (alternative) as shown in the embodiments of FIGS. 7, 8, and 9) to the arterial vasculature of the patient.

If the above-described optional monitoring/control console 15 is to be utilized, such console 15 will be positioned within the operating room and, if necessary, will be preprogrammed with the appropriate patient/procedure information. The monitoring/control console 15 may additionally be connected to the separate temperature control apparatus TCA which is being utilized to provide temperature-controlled heat exchange fluid (e.g., warm water) to the system 10 as well as the oxygen/air blending apparatus BA which is being utilized to provide oxygen or oxygen-enriched air to the system 10. In this regard, a single monitoring/control console 15 may be utilized to control some or all of the operational variables and parameters of the system and/or to monitor the inputs received from the various sensors (e.g., blood pH, blood $pCO_2$, blood $pO_2$, blood temperature, blood flow rate, $FiO_2$, gas temperature, gas flow rate, water temperature, water flow rate, pump speed, electrical power input, etc.) for which sensors (not shown) are mounted within the system 10.

Additionally, the monitoring/control console 15 may incorporate a computer or microprocessor which is programmed to cause the system 10 to operate in a predetermined manner, with appropriate changes or modifications in the operational variables of the system as required by the particular patient, or as dictated by the type of operative procedure which is being performed on the patient.

Irrespective of whether the M/D component 14, temperature control apparatus TCA and air/oxygen blending apparatus BA are being manually set and controlled independently, or commonly set and controlled by way of a single monitoring/control console 15, the motor located within the base 13 of the M/D component will be energized and caused to rotate in a first direction, thereby causing the pump impeller assembly 38 to be driven in a clockwise direction. The rotating helical vanes 94 of the impeller 40 will axially pull or draw the blood downwardly from the blood inlet port 28, and will feed the blood into the areas in front of the leading surfaces 100 of the centrifugal propulsion legs 98 of the impeller 40. The moving centrifugal propulsion legs 98 of the impeller 40 will then centrifugally propel the blood, outwardly, through outflow space 52 and into the individual cylindrical segments of the heat exchange cavity 50.

As the blood passes downwardly through the outer helical troughs 60 of the heat exchange tubes 54, the contact of the blood with the outer surfaces of the heat exchange tubes 54 will cause the temperature of the blood to become equilibrated with the temperature of the temperature-control water which is being passed upwardly through the heat exchange tubes 54.

Thereafter, as the blood reaches the bottom end of the segmented heat exchange cavity 50, the blood will pass out of the second blood outflow space 70 and into the cylindrical gas exchange space 72 of the membrane oxygenator portion of the system. The blood will flow downwardly over the outer surfaces of the gas exchange membranes 74. Carbon dioxide of the blood will diffuse through the walls of the membranes 74 and into the gas which is being passed through the lumens of the membrane 74, and oxygen contained within the gas will diffuse outwardly through the walls of the membranes, into the blood. In this regard, the $pCO_2$ and $pO_2$ of the blood will be adjusted to the desired arterial valves, and resultant changes will occur in the pH of the blood in accordance with the alteration of the $pCO_2$ therein. Also, the contact of the flowing blood with the heat transfer wall 109 which separates the gas exchange cavity 72 from the adjacent cylindrical heat exchange fluid flow space 107 will cause the temperature of the blood to be maintained in equilibration with the temperature of the water which is flowing upwardly through cylindrical heat exchange fluid flow space 107. This aspect of the invention will deter or prevent the temperature of the blood from falling or decreasing as it passes downwardly, through the membrane oxygenator portion of the system 10.

The exiting gas, which contains the $CO_2$ which has been received from the blood, along with any excess $O_2$ or air, will then flow out of gas outlet 82, into the atmosphere.

The arterial blood, having passed through the oxygenator, and having acquired the desired partial pressures of $CO_2$ and $O_2$, will then flow out of the blood outlet 88 (and/or through any arterial filter element 128 incorporated as in the embodiments shown in FIGS. 8–8a or any separate in-line arterial filter which may be attached to the line) and will be returned to the arterial vasculature of the patient through the arterial blood return tube.

It will be appreciated that the invention has been described hereabove with reference to certain presently preferred embodiments only, and no effort has been made to exhaustively describe all possible embodiments in which the invention may be formed. Any and all specific elements described herein with respect to a single embodiment may be interchanged with, or utilized in connection with, any other embodiment. Various additions deletions and modifications may be made to the above-described described embodiments without departing from the intended spirit and scope of the invention. Accordingly, it is intended that all such additions, deletions and modifications be included within the scope of the following claims.

What is claimed is:

1. An extracorporeal blood oxygenation system comprising:
   (a) an integrated blood pump/heat exchanger/membrane oxygenator component comprising:
      i) a blood pump;
      ii) a heat exchanger positioned below said blood pump;
      iii) a membrane oxygenator positioned below said heat exchanger;
      said blood pump, heat exchanger, and membrane oxygenator being joined to one another as a unitary integrated assembly having a bottom end and a top end, said integrated assembly having an opening formed in the bottom end thereof and a hollow inner cavity formed within, said hollow inner cavity extending upwardly from said opening,
      said integrated assembly further having a blood inlet port formed therein for passing blood into said pump, a blood outlet port formed therein for allowing blood to pass out of said membrane oxygenator, and a blood flow path formed within said assembly, between said inlet port and said outlet port, wherein blood entering said blood inlet port passes initially downward through said pump, then downward through said heat exchanger, then downward through said membrane oxygenator, and out of said blood outlet port,
      said blood pump comprising:
         i) a pump housing having said blood inlet port formed at the top end thereof and a pump housing outlet at the bottom end thereof, said pump housing outlet forming a radially outwardly directed passageway from said pump housing into said heat exchanger;
         ii) a blood pump impeller positioned within said pump housing, said impeller comprising:
         iii) a plurality of centrifugal propulsion legs which extend outwardly from a vertical rotational axis, each of said centrifugal propulsion legs having a leading surface and a trailing surface; and
         iv) a plurality of helical strut members which extend from said centrifugal propulsion legs, said strut members being helically disposed about said vertical rotational axis; and
         v) a central member which is coaxial with said rotational axis, said central member extending and upwardly from said centrifugal propulsion legs, said helical strut members being helically twined about and spaced apart from said central member;
      said impeller being thereby configured such that, when said impeller is rotated in a first direction about said axis, said helical strut members axially draw blood from said blood inlet, in a downward direction, such that blood deposits in front of the leading surfaces of said centrifugal propulsion legs, the rotational movement of said centrifugal propulsion legs being thereby operative to radially propel the blood out of said pumping housing outlet and into said heat exchanger,
   (b) a motor/drive component comprising:
      i) a base housing having an electric motor located therewithin;
      ii) a support projection which extends upwardly from said base housing, said support projection being insertable through said opening and into the hollow inner cavity of said blood pump/heat exchanger/membrane oxygenator component;
      iii) a rotatable drive member which extends upwardly through said support projection, said drive member being rotatably driven by said motor;
   said blood pump/heat exchanger/membrane oxygenator component being positionable upon the motor/drive component such that the support projection of said motor/drive component extends into and is received within the hollow inner cavity of the blood pump/heat exchanger/membrane oxygenator component, and further such that the drive member rotatably engages said blood pump.

2. The system of claim 1 wherein said blood pump/heat exchanger/membrane oxygenator component is of disposable construction and wherein said motor/drive component is of reusable construction.

3. The system of claim 1 wherein said pump impeller further comprises:
   said central member having a blunt top end and a bottom end, the blunt top end of said central member being smaller in diameter than the bottom end thereof.

4. The system of claim 1 wherein said helical vanes are free standing except for attachment to said centrifugal propulsion legs, and are unconnected to said central member.

5. The system of claim 1 wherein said helical vanes are formed independently of one another and are free-standing accept for points of attachment to the respective centrifugal propulsion legs of said impeller.

6. The system of claim 1 wherein said helical vanes have helical undersurfaces which are substantially parallel to one another.

7. The system of claim 1 wherein said helical vanes are substantially coextensive with one another, and have upper ends, the upper ends of said vanes lying in a common horizontal plane and being spaced equidistantly from said vertical rotational axis of said impeller.

8. The system of claim 1 wherein said leading surfaces of said centrifugal propulsion legs are larger than the trailing surfaces thereof.

9. The system of claim 1 wherein indentations are formed in the leading surfaces of said centrifugal propulsion legs.

10. The system of claim 1 wherein the leading surfaces of said centrifugal propulsion legs have lengths of approximately 1.24 cm and the trailing surfaces thereof have lengths of approximately 0.62 cm.

11. The system of claim 1 wherein said heat exchanger comprises:

a heat exchanger housing portion having a heat exchange cavity defined therewithin;

a plurality of heat exchange tubes which are substantially parallel to one another and which extend vertically through said heat exchange cavity;

a heat exchanger blood inlet at the top of said heat exchange cavity and a heat exchanger blood outlet at the bottom of said heat exchange cavity;

a heat exchange fluid inlet for passing temperature-controlled heat exchange fluid into said heat exchange tubes and a heat exchange fluid outlet for allowing said heat exchange fluid to pass out of the lumens of said heat exchange tubes;

heat exchange fluid being thereby passable through the lumens of said heat exchange tubes concurrently with the passage of blood through said heat exchange cavity and in contact with said heat exchange tubes, thereby resulting in temperature control of the blood.

12. The system of claim 11 wherein each of said heat exchange tubes has a longitudinal axis, an outer surface and an inner surface, and wherein each heat exchange tube is twisted about its longitudinal axis such that helical ribs are formed on the inner and outer surfaces thereof, and further such that inner and outer helical troughs are defined between adjacent ones of said inner and outer helical ribs.

13. The system of claim 12 wherein rod members extend coaxially through the lumens of the heat exchange tubes so as to occupy space within the center of each lumen, thereby causing heat exchange fluid to flow around said rods and in contact with the inner surfaces of said heat exchange tubes.

14. The system of claim 11 wherein said heat exchanger housing portion is constructed so as to substantially partition said heat exchange cavity into a plurality of generally cylindrical tube enclosures, said enclosures being arranged in a generally cylindrical array about said vertical rotational axis and being substantially parallel to one another, each of said enclosures extending substantially around one of said heat exchange tubes, thereby causing blood which flows through said heat exchange cavity to be selectively channelled into contact with outer surfaces of said heat exchange tube.

15. The system of claim 12 wherein said heat exchanger housing portion is constructed so as to substantially partition said heat exchange cavity into a plurality of cylindrical substantially surround and come in contact with the helical outer ribs of said heat exchange tubes such that blood which is flowing downwardly through said heat exchange cavity will be channeled through the outer helical troughs defined between the adjacent ones of said outer helical ribs of said heat exchange tubes.

16. The system of claim 11 wherein said heat exchange tubes have outer diameters of 3/8"–1/2" and are mounted within said heat exchange cavity.

17. The system of claim 1 wherein said membrane oxygenator comprises:

an oxygenator housing having a generally cylindrical gas exchange cavity formed therein;

a plurality of tubular gas exchange membranes disposed within said gas exchange cavity, each of said gas exchange membranes having an inner surface, an outer surface and a hollow lumen extending longitudinally therethrough;

an oxygenator blood inlet formed at the top of said gas exchange cavity and an oxygenator blood outlet at the bottom of said gas exchange cavity such that blood may be passed generally downwardly through said gas exchange cavity in contact with the outer surfaces of said hollow fiber membranes;

a gas inlet for passing gas into the lumens of said hollow fiber membranes and a gas outlet for allowing gas to pass out of the lumens of said hollow fiber membranes;

said membrane oxygenator being thereby operative to remove $CO_2$ from the blood and to impart $O_2$ to the blood as blood is circulated over the outer surfaces of said hollow fiber membranes concurrently with the flow of gas through the lumens of said hollow fiber membranes.

18. The system of claim 1 wherein said integrated blood pump/heat exchanger/membrane oxygenator component further comprises:

iv) a blood reservoir rigidly joined to said blood pump, said reservoir being constructed to receive and collect blood prior to passage of said blood into said blood pump.

19. The system of claim 1 wherein said integrated blood pump/heat exchanger/membrane oxygenator component further comprises:

a blood reservoir housing portion formed above said pump housing portion and defining therewithin a blood reservoir cavity, said blood reservoir housing portion having a reservoir blood inlet formed therein to permit blood to be passed into said blood reservoir cavity, and a reservoir blood outlet which leads into the blood inlet port at the top end of said pump housing such that blood may flow from said blood reservoir cavity into said hollow pump impeller cavity.

20. The system of claim 1 wherein said integrated blood pump/heat exchanger/membrane oxygenator component further comprises:

iv) an arterial filter rigidly joined to said membrane oxygenator for filtering the blood after the blood has passed through the membrane oxygenator.

21. The system of claim 20 wherein said arterial filter comprises a) an arterial filter housing and b) a blood permeable filter element disposed within said housing.

22. The system of claim 21 wherein said arterial filter further comprises a bypass valving apparatus which is alternately positionable:

in a first position wherein said valving apparatus will cause the blood to pass through said filter element; and, a second position wherein said valving apparatus will cause the blood to bypass said filter element.

23. The system of claim 1 wherein said blood pump/heat exchanger/membrane oxygenator component further comprises:

an arterial filter housing portion formed adjacent said membrane oxygenator housing portion, said arterial filter housing portion defining therewithin an arterial filter cavity;

an arterial filter element disposed within said arterial filter cavity for filtering blood which passes therethrough;

said third blood outlet being a passageway from said gas exchange cavity into said arterial filter cavity such that blood which has passed through said gas exchange cavity will then pass into said arterial filter cavity and through said arterial filter; and, a fourth blood outlet to allow blood to pass out of said arterial filter cavity and to be returned to said patient.

24. The system of claim 23 wherein said system further comprises:

a bypass valving apparatus associated with said arterial filter cavity, said bypass valving apparatus being alternately positionable in:
   i) a first position wherein said valving apparatus will cause the blood to flow through said arterial filter element; and,
   ii) a second position wherein said valving apparatus will cause said blood to bypass said arterial filter element and will flow out of said fourth blood outlet without having passed through said arterial filter element.

25. The system of claim 1 wherein said system further comprises:

a heat exchange fluid passageway which is located adjacent said membrane oxygenator, said heat exchange fluid passageway being connected to said heat exchange tubes such that the passage of heat exchange fluid through said heat exchange tubes will concurrently result in the passage of heat exchange fluid through said heat exchange fluid passageway; and, a temperature transfer wall seperating said heat exchange fluid passageway from said membrane oxygenator such that the temperature of blood flowing through said membrane oxygenator will tend to equilibrate with the temperature of heat exchange fluid passing through said heat exchange fluid passageway.

26. The system of claim 25 wherein said inner cavity of said blood pump/heat exchanger/membrane oxygenator component is generally cylindrical in configuration, and wherein said heat exchange fluid passageway comprises a generally cylindrical cavity which is formed around said hollow inner cavity, and inboard of said membrane oxygenator gas exchange cavity.

27. The system of claim 1 wherein the pump housing defines therewithin a blood pump impeller housing chamber, and wherein a rotatable drive shaft is attached to and extends from said pump impeller, through at least a portion of said pump housing, and wherein said system further comprises:

a seal assembly which is mounted in contact with at least a portion of said pump housing, and which forms a substantially fluid tight seal against one of said blood pump impeller and said impeller drive shaft so as to prevent leakage of blood out of said pump housing, said seal assembly comprising:
   an annular chevron-type seal having an annular v-shaped groove extending thereabout; and,
   a rigid ring member having an annular v-shaped projection extending from one side thereof, said ring member being juxtapositioned to said seal member such that the v-shaped projection of said ring member is inserted within the v-shaped groove of said seal member.

28. The system of claim 27 wherein said ring member is formed of material which is suitable for blood contact, and wherein a portion of said ring member extends into said blood pump impeller cavity such that it will come into contact with blood contained within said blood pump impeller cavity.

* * * * *